(12) United States Patent
Green et al.

(10) Patent No.: US 7,345,088 B2
(45) Date of Patent: Mar. 18, 2008

(54) PHARMACEUTICAL COMPOSITION FOR USE FOR THE TREATMENT OF MALIGNANCIES COMPRISING IN COMBINATION A BISPHOSPHONATES, A COX-2 INHIBITOR AND A TAXOL

(75) Inventors: Jonathan Green, Arlesheim (CH); Allan Lipton, Hershey, PA (US); Lois Mary Witters, York Haven, PA (US)

(73) Assignees: Penn State Research Foundation, University Park, PA (US); Novartis AG, Basel (CH)

( * ) Notice: Subject to any disclaimer, the term of this patent is extended or adjusted under 35 U.S.C. 154(b) by 130 days.

(21) Appl. No.: 10/493,042

(22) PCT Filed: Oct. 18, 2002

(86) PCT No.: PCT/EP02/11696

§ 371 (c)(1),
(2), (4) Date: Aug. 23, 2004

(87) PCT Pub. No.: WO03/035081

PCT Pub. Date: May 1, 2003

(65) Prior Publication Data

US 2005/0014726 A1 Jan. 20, 2005

Related U.S. Application Data

(60) Provisional application No. 60/345,921, filed on Oct. 19, 2001.

(51) Int. Cl.
*A61K 31/335* (2006.01)
(52) U.S. Cl. ..................................................... 514/449
(58) Field of Classification Search ................... 514/89
See application file for complete search history.

(56) References Cited

FOREIGN PATENT DOCUMENTS

| WO | WO 00 38730 | 7/2000 |
|----|-------------|--------|
| WO | WO 01 54688 | 8/2001 |

OTHER PUBLICATIONS

Witters et al., "Inhibition of Growth of Human Breast Cancer Cell Lines with the Combination of Zoledronic Acid and a COX-2 Inhibitor", European Journal of Cancer, vol. 37, No. Suppl. 6, p. 78, (2001).
Urban et al., "Antinociceptive Effects of the Bisphosphonate, Zoledronate, in a Novel Rat Model of Bone Cancer Pain", Society for Neuroscience Abstracts, vol. 27, No. 1, p. 1326, 31st Annual Meeting of the Society for Neuroscience, San Diego, Ca, (2001).
McDonnell, et al, "Advances in Cancer Pain Management", Current Oncology Reports, vol. 2, No. 4, pp. 351-357, (2000).
Gloth, F. M. "Pain Management in Older Adults: Prevention and Treatment", Journal of the American Geriatrics Society, vol. 49, No. 3, pp. 188-199, (2001).
Soriano et al., "Synergistic Effects of New Chemopreventitive Agents and Conventional Cytotoxic Agents Against Human Lung Cancer Cell Lines", Cancer Research, American Association for Cancer Research, Baltimore, MD, vol. 59, pp. 6178-6184, (1999).
Oura et al., Databse Cancerlit 'Online!"Effective Alendronate Therapy Against a Bone Metastasis Occurring during Docetaxel Therapy for Breast Cancer-a Case Report", Database Accession No. 1999430323 & Dan To Kagaku Ryoho, Japanese Journal of Cancer and Chemotherapy! (1999).
Jagdev et al., "The Bisphosphonate, Zoledronic Acid, Induces Apoptosis of Breast Cancer Cells: Evidence of Synergy with Paclitaxel" British Journal of Cancer, London, vol. 8, No. 84, pp. 1126-1134, (2001).
Magnetto et al., "Addictive Antitumor Activities of Taxoids in Combination with the Bisphosphonate Ibandronate Against Invasion and Adhesion of Human Breast Carcinoma Cells to Bone", International Journal of Cancer, vol. 83, pp. 263-269, (1999).

*Primary Examiner*—Ardin H. Marschel
*Assistant Examiner*—James D. Anderson
(74) *Attorney, Agent, or Firm*—Oona A. Manzari

(57) ABSTRACT

A pharmaceutical composition for treatment of malignancies, in particular a malignant disease which is associated with the development of bone metastases or excessive bone resorption, comprises in combination a bisphosphonates, COX-2 inhibitor and/or a taxol or derivative thereof for simultaneous, sequential or separate use. Also provided is a method of treating a patient suffering from a malignant disease comprising administering to the patient an effective amount of a bisphosphonates, an effective amount of a COX-2 inhibitor and/or and effective amount of a taxol or derivative thereof.

2 Claims, No Drawings

PHARMACEUTICAL COMPOSITION FOR USE FOR THE TREATMENT OF MALIGNANCIES COMPRISING IN COMBINATION A BISPHOSPHONATES, A COX-2 INHIBITOR AND A TAXOL

This invention relates to bisphosphonates, in particular to new pharmaceuticals uses of, and compositions containing, bisphosphonates.

Bisphosphonates are widely used to inhibit osteoclast activity in a variety of both benign and malignant diseases, which involve excessive or inappropriate bone resorption. These pyrophosphate analogs not only reduce the occurrence of skeletal related events but they also provide patients with clinical benefit and improve survival. Bisphosphonates are able to prevent bone resorption in vivo; the therapeutic efficacy of bisphosphonates has been demonstrated in the treatment of osteoporosis, osteopenia, Paget's disease of bone, tumour-induced hypercalcemia (TIH) and, more recently, bone metastases (BM) and multiple myeloma (MM) (for review see Fleisch H 1997 Bisphosphonates clinical. In Bisphosphonates in Bone Disease. From the Laboratory to the Patient. Eds: The Parthenon Publishing Group, New York/London pp 68-163). The mechanisms by which bisphosphonates inhibit bone resorption are still not completely understood and seem to vary according to the bisphosphonates studied. Bisphosphonates have been shown to bind strongly to the hydroxyapatite crystals of bone, to reduce bone turn-over and resorption, to decrease the levels of hydroxyproline or alkaline phosphatase in the blood, and in addition to inhibit the formation, recruitment, activation and the activity of osteoclasts.

Recent studies have also shown that some bisphosphonates may have a direct effect on tumour cells. Thus for example it has been found that relatively high concentrations of bisphosphonates, including zoledronate, induce apoptosis of breast and prostate carcinoma and myeloma cells in vitro (Senaratne et al. Br. J. Cancer, 82: 1459-1468, 2000; Lee et al., Cancer Res., 61: 2602-2608, 2001, Shipman et al. Br. J. Cancer, 98: 665-672 (1997).

It has now been found that if certain types of bisphosphonates are used in combination with certain types of cyclooxgenase-2 (COX-2) inhibitors to treat cancer cells in vitro, that enhanced, and in some cases synergistic, cell growth inhibition is achieved compared with use of either the bisphosphonate or COX-2 inhibitor alone.

Accordingly the present invention provides a pharmaceutical composition for treatment of malignancies, which comprises in combination a bisphosphonate and a COX-2 inhibitor for simultaneous, sequential or separate use.

Further the invention provides the use of a COX-2 inhibitor for the preparation of a medicament, for use in combination with a bisphosphonate for treatment of a malignant disease.

In the alternative the invention provides use of a bisphosphonate for the preparation of a medicament for use in combination with a COX-2 inhibitor for treatment of a malignant disease.

In a further aspect the invention provides a method of treating a patient suffering from a malignant disease comprising administering to the patient an effective amount of a bisphosphonate and an effective amount of a COX-2 inhibitor.

Yet further the invention provides use of a COX-2 inhibitor in combination with a bisphosphonate to inhibit cancer cell growth or induce cancer cell apoptosis.

Accordingly also the present invention further provides a pharmaceutical composition for inhibiting cancer cell growth or inducing cancer cell apoptosis which comprises in combination a bisphosphonate and COX-2 inhibitor for simultaneous, sequential or separate use.

Further the invention provides the use of a bisphosphonate for the preparation of a medicament, for use in combination with a COX-2 inhibitor for inhibiting cancer cell growth or inducing cancer cell apoptosis.

In preferred embodiments the bisphosphonate and COX-2 inhibitor are used in combination with Taxol or a derivative thereof.

Accordingly in a yet further aspect the present invention also provides a pharmaceutical composition for treatment of malignancies, which comprises in combination a bisphosphonate, Taxol or a derivative thereof and a COX-2 inhibitor for simultaneous, sequential or separate use.

Further the invention provides the use of a Taxol or a derivative thereof for the preparation of a medicament, for use in combination with a bisphosphonate and a COX-2 inhibitor for treatment of a malignant disease.

Further still the invention provides a method of treating a patient suffering from a malignant disease comprising administering to the patient an effective amount of a bisphosphonate, an effective amount of a COX-2 inhibitor and an effect amount of a Taxol or a derivative thereof.

In accordance with the present invention it has been found that all possible double combinations of a) bisphosphonates, b) COX-2 inhibitor and c) Taxol or derivative thereof, as tested, gave enhanced growth inhibition of cancer cells when compared with use of each agent separately.

Thus in yet further embodiments the invention provides:
a method of treating a patient suffering from a malignant disease comprising administering to the patient an effective amount of a Taxol or a derivative thereof in combination with an effect amount of a bisphosphonate or an effective amount of a COX-2 inhibitor;
a corresponding pharmaceutical composition for simultaneous, sequential or separate use; and uses of the corresponding dual combinations, i.e. taxol or derivative thereof+bisphosphonate, or taxol or derivative thereof+COX-2 inhibitor, for the preparation of anti-cancer medicaments.

In the present description the term "treatment" includes both prophylactic or preventative treatment as well as curative or disease modifying treatment, including treatment of patients at risk of contracting the disease or suspected to have contracted the disease as well as ill patients.

The invention is generally applicable to the treatment of malignant diseases for which bisphosphonate treatment is indicated. Thus typically the disease is a malignant disease which is associated with the development of bone metastases or excessive bone resorption. Examples of such diseases include cancers, such as breast and prostate cancers, multiple myeloma (MM), tumour induced hypertension (TIH) and similar diseases and conditions. In particular the invention is applicable to the treatment of bone metastases (BM) associated with cancers such as breast cancer, lung cancer, colon cancer or prostate cancer.

The compositions, uses and methods of the present invention represent an improvement to existing therapy of malignant diseases in which bisphosphonates are used to prevent or inhibit development of bone metastases or excessive bone resorption, and in which (as has been discovered in accordance with the present invention) bisphosphonate treatment also inhibits cancer cell growth or induces cancer cell apoptosis. The combination of a bisphosphonate with a COX-2 inhibitor, especially also with Taxol or a derivative thereof, advantageously gives rise to enhanced, or even synergistic, levels of cancer cell growth inhibition or cancer cell apoptosis.

The bisphosphonates for use in the present invention are preferably N-bisphosphonates.

For the purposes of the present description an N-bisphosphonate is a compound which in addition to the characteristic geminal bisphosphate moiety comprises a nitrogen containing side chain, e.g. a compound of formula I

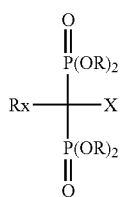

wherein

X is hydrogen, hydroxyl, amino, alkanoyl,or an amino group substituted by $C_1$-$C_4$ alkyl or alkanoyl;

R is hydrogen or $C_1$-$C_4$ alkyl and

Rx is a side chain which contains an optionally substituted amino group, or a nitrogen containing heterocycle (including aromatic nitrogen-containing heterocycles), and pharmaceutically acceptable salts thereof or any hydrate thereof.

Thus, for example, suitable N-bisphosphonates for use in the invention may include the following compounds or a pharmaceutically acceptable salt thereof, or any hydrate thereof: 3-amino-1-hydroxypropane-1,1-diphosphonic acid (pamidronic acid), e.g. pamidronate (APD); 3-(N,N-dimethylamino)-1-hydroxypropane-1,1-diphosphonic acid, e.g. dimethyl-APD; 4-amino-1-hydroxybutane-1,1-diphosphonic acid (alendronic acid), e.g. alendronate; 1-hydroxy-3-(methylpentylamino)-propylidene-bisphosphonic acid, ibandronic acid, e.g. ibandronate; 6-amino-1-hydroxyhexane-1,1-diphosphonic acid, e.g. amino-hexyl-BP; 3-(N-methyl-N-n-pentylamino)-1-hydroxypropane-1,1-diphosphonic acid, e.g. methyl-pentyl-APD (=BM 21.0955); 1-hydroxy-2-(imidazol-1-yl)ethane-1,1-diphosphonic acid, e.g. zoledronic acid; 1-hydroxy-2-(3-pyridyl)ethane-1,1-diphosphonic acid (risedronic acid), e.g. risedronate, including N-methyl pyridinium salts thereof, for example N-methyl pyridinium iodides such as NE-10244 or NE-10446; 3-[N-(2-phenylthioethyl)-N-methylamino]-1-hydroxypropane-1,1-di-phosphonic acid; 1-hydroxy-3-(pyrrolidin-1-yl) propane-1,1-diphosphonic acid, e.g. EB 1053 (Leo); 1-(N-phenylaminothiocarbonyl)methane-1,1-diphosphonic acid, e.g. FR 78844 (Fujisawa); 5-benzoyl-3,4-dihydro-2H-pyrazole-3,3-diphosphonic acid tetraethyl ester, e.g. U-81581 (Upjohn); and 1-hydroxy-2-(imidazo[1,2-a]pyridin-3-yl)ethane-1,1-diphosphonic acid, e.g. YM 529.

In one embodiment a particularly preferred N-bisphosphonate for use in the invention comprises a compound of Formula II

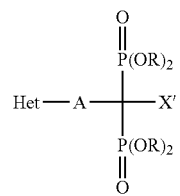

wherein

Het is an imidazole, oxazole, isoxazole, oxadiazole, thiazole, thiadiazole, pyridine, 1,2,3-triazole, 1,2,4-triazole or benzimidazole radical which is optionally substituted by alkyl alkoxy, halogen, hydroxyl carboxyl, an amino group optionally substituted by alkyl or alkanoyl radicals or a benzyl radical optionally substituted by alkyl, nitro, amino or aminoalkyl;

A is a straight-chained or branched, saturated or unsaturated hydrocarbon moiety containing from 1 to 8 carbon atoms;

X' is a hydrogen atom, optionally substituted by alkanoyl, or an amino group optionally substituted by alkyl or alkanoyl radicals, and R is a hydrogen atom or an alkyl radical, and the pharmacologically acceptable salts thereof.

In a further embodiment a particularly preferred bisphosphonate for use in the invention comprises a compound of Formula III

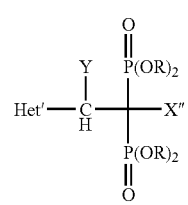

wherein

Het' is a substituted or unsubstituted heteroaromatic five-membered ring selected from the group consisting of imidazolyl, imidazolinyl, isoxazolyl, oxazolyl, oxazolinyl, thiazolyl thiazolinyl, triazolyl oxadiazolyl and thiadiazolyl wherein said ring can be partly hydrogenated and wherein said substituents are selected from at least one of the group consisting of $C_1$-$C_4$ alkyl $C_1$-$C_4$ alkoxy, phenyl, cyclohexyl, cyclohexylmethyl, halogen and amino and wherein two adjacent alkyl substituents of Het can together form a second ring;

Y is hydrogen or $C_1$-$C_4$ alkyl;

X" is hydrogen, hydroxyl, amino, or an amino group substituted by $C_1$-$C_4$ alkyl, and R is hydrogen or $C_1$-$C_4$ alkyl; as well as the pharmacologically acceptable salts and isomers thereof.

In a yet further embodiment a particularly preferred bisphosphonate for use in the invention comprises a compound of Formula IV

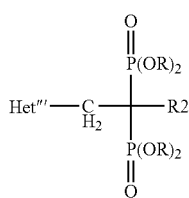

(IV)

wherein
Het''' is an imidazolyl, 2H-1,2,3-, 1H-1,2,4- or 4H-1,2,4-triazolyl, tetrazolyl, oxazolyl, isoxazolyl, oxadiazolyl, thiazolyl or thiadiazolyl radical which is unsubstituted or C-mono- or di-substituted by lower alkyl, by lower alkoxy, bx phenyl which may in turn be mnon- or disubstituted by lower alkyl, lower alkoxy and/or halogen, by hydroxy, by di-lower alkylamino, by lower alkylthio and/or by halogen and is N-substituted at a substitutable N-atom by lower alkyl or by phenyl-lower alkyl which may in turn be mono- or di-substituted in the phenyl moiety by lower alkyl, lower alkoxy and/or halogen, and R2 is hydrogen, hydroxy, amino, lower alkylthio or halogen, lower radicals having up to and including 7 C-atoms, or a pharmacologically acceptable salt thereof.

Examples of particularly preferred N-bisphosphonates for use in the invention are:

2-(1-Methylimidazol-2-yl)-1-hydroxyethane-1,1-diphosphonic acid;
2-(1-Benzylimidazol-2-yl)-1-hydroxyethane-1,1-diphosphonic acid;
2-(1-Methylimidazol-4-yl)-1-hydroxyethane-1,1-diphosphonic acid;
1-Amino-2-(1-methylimidazol-4-yl)ethane-1,1-diphosphonic acid;
1-Amino-2-(1-benzylimidazol-4-yl)ethane-1,1-diphosphonic acid;
2-(1-Methylimidazol-2-yl)ethane-1,1-diphosphonic acid;
2-(1-Benzylimidazol-2-yl)ethane-1,1-diphosphonic acid;
2-(Imidazol-1-yl)-1-hydroxyethane-1,1-diphosphonic acid;
2-(Imidazol-1-yl)ethane-1,1-diphosphonic acid;
2-(4H-1,2,4-triazol-4-yl)-1-hydroxyethane-1,1-diphosphonic acid;
2-(Thiazol-2-yl)ethane-1,1-diphosphonic acid;
2-(Imidazol-2-yl)ethane-1,1-diphosphonic acid;
2-(2-Methylimidazol-4(5)-yl)ethane-1,1-diphosphonic acid;
2-(2-Phenylimidazol-4(5)-yl)ethane-1,1-diphosphonic acid;
2-(4,5-Dimethylimidazol-1-yl)-1-hydroxyethane-1,1-diphosphonic acid, and
2-(2-Methylimidazol-4(5)-yl)-1-hydroxyethane-1,1-diphosphonic acid, and pharmacologically acceptable salts thereof.

The most preferred N-bisphosphonate for use in the invention is 2-(imidazol-1yl)-1-hydroxyethane-1,1-diphosphonic acid (zoledronic acid) or a pharmacologically acceptable salt thereof.

All the N-bisphosphonic acid derivatives mentioned above are well known from the literature. This includes their manufacture (see e.g. EP-A-513760, pp. 13-48). For example, 3-amino-1-hydroxypropane-1,1-diphosphonic acid is prepared as described e.g. in U.S. Pat. No. 3,962,432 as well as the disodium salt as in U.S. Pat. Nos. 4,639,338 and 4,711,880, and 1-hydroxy-2-(imidazol-1-yl)ethane-1,1-diphosphonic acid is prepared as described e.g. in U.S. Pat. No. 4,939,130. See also U.S. Pat. Nos. 4,777,163 and 4,687,767.

The N-bisphosphonates may be used in the form of an isomer or of a mixture of isomers where appropriate, typically as optical isomers such as enantiomers or diastereoisomers or geometric isomers, typically cis-trans isomers. The optical isomers are obtained in the form of the pure antipodes and/or as racemates.

The N-bisphosphonates can also be used in the form of their hydrates or include other solvents used for their crystallisation.

The COX-2 inhibitors used in the pharmaceutical compositions and treatment methods of the present invention are typically those which have an $IC_{50}$ for COX-2 inhibition less than about 2 μM and an $IC_{50}$ for COX-1 inhibition greater than about 5 μM, e.g. when measured in the assays described by Brideau et al.in Inflamm. Res. 45:68-74 (1996). Preferably the COX-2 inhibitor has a selectivity ratio of at least 10, more preferably at least 40, for COX-2 inhibition over COX-1 inhibition.

Thus, for example, suitable COX-2 inhibitors for use in the invention may include the following compounds or derivatives thereof or a pharmaceutically acceptable salt thereof, or any hydrate thereof: rofecoxib, etoricoxib, celecoxib, valdecoxib, parecoxib, or a 5-alkyl-2-arylaminophenylacetic acid derivative COX-2 inhibitor, e.g. of formula V as defined below.

In an embodiment a COX-2 inhibitor for use in the present invention comprises a compound of formula V

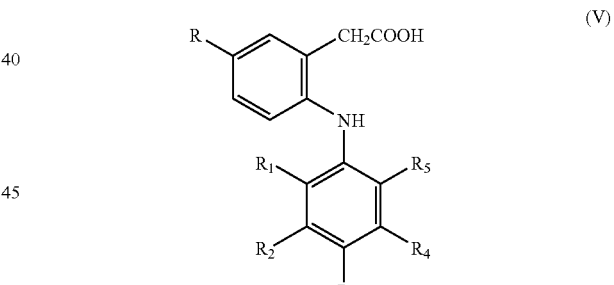

(V)

wherein R is methyl or ethyl;
$R_1$ is chloro or fluoro;
$R_2$ is hydrogen or fluoro;
$R_3$ is hydrogen, fluoro, chloro, methyl, ethyl, methoxy, ethoxy or hydroxy;
$R_4$ is hydrogen or fluoro; and
$R_5$ is chloro, fluoro, trifluoromethyl or methyl;
pharmaceutically acceptable salts thereof; and
pharmaceutically acceptable prodrug esters thereof.

Particular compounds of formula V are those wherein R is methyl or ethyl; $R_1$ is chloro or fluoro; $R_2$ is hydrogen; $R_3$ is hydrogen, fluoro, chloro, methyl or hydroxy; $R_4$ is hydrogen; and $R_5$ is chloro, fluoro or methyl; pharmaceutically acceptable salts thereof; and pharmaceutically acceptable esters thereof.

A particular embodiment relates to the compounds of formula V wherein R is methyl or ethyl; $R_1$ is fluoro; $R_2$ is hydrogen; $R_3$ is hydrogen, fluoro or hydroxy; $R_4$ is hydrogen; and $R_5$ is chloro; pharmaceutically acceptable salts thereof; and pharmaceutically acceptable prodrug esters thereof.

Another particular embodiment of the invention relates to compounds of formula V wherein R is ethyl or methyl; $R_1$ is fluoro; $R_2$ is hydrogen or fluoro; $R_3$ is hydrogen, fluoro, ethoxy or hydroxy; $R_4$ is hydrogen or fluoro; and $R_5$ is chloro, fluoro or methyl; pharmaceutically acceptable salts thereof; and pharmaceutically acceptable prodrug esters thereof.

Further are said compounds wherein R is methyl or ethyl; $R_1$ is fluoro; $R_2$-$R_4$ are hydrogen or fluoro; and $R_5$ is chloro or fluoro; pharmaceutically acceptable salts thereof; and pharmaceutically acceptable prodrug esters thereof.

A further embodiment of the invention relates to the compounds of formula V wherein R is methyl or ethyl; $R_1$ is fluoro; $R_2$ is fluoro; $R_3$ is hydrogen, ethoxy or hydroxy; $R_4$ is fluoro; and $R_5$ is fluoro; pharmaceutically acceptable salts thereof; and pharmaceutically acceptable prodrug esters thereof.

Another embodiment of the invention relates to the compounds of formula V wherein R is methyl; $R_1$ is fluoro; $R_2$ is hydrogen; $R_3$ is hydrogen or fluoro; $R_4$ is hydrogen; and $R_5$ is chloro; pharmaceutically acceptable salts thereof; and pharmaceutically acceptable prodrug esters thereof.

Particular embodiments of the invention relate to compounds of formula V
  (a) wherein R is methyl; $R_1$ is fluoro; $R_2$ is hydrogen; $R_3$ is hydrogen; $R_4$ is hydrogen; and $R_5$ is chloro; pharmaceutically acceptable salts thereof; and pharmaceutically acceptable prodrug esters thereof;
  (b) wherein R is methyl; $R_1$ is fluoro; $R_2$ is hydrogen; $R_3$ is fluoro; $R_4$ is hydrogen; and $R_5$ is chloro; pharmaceutically acceptable salts thereof; and pharmaceutically acceptable prodrug esters thereof;
  (c) wherein R is ethyl; $R_1$ is fluoro; $R_2$ is fluoro; $R_3$ is hydrogen; $R_4$ is fluoro; and $R_5$ is fluoro; pharmaceutically acceptable salts thereof; and pharmaceutically acceptable prodrug esters thereof; and
  (d) wherein R is ethyl; $R_1$ is chloro; $R_2$ is hydrogen; $R_3$ is chloro; $R_4$ is hydrogen; and $R_5$ is methyl; pharmaceutically acceptable salts thereof; and pharmaceutically acceptable prodrug esters thereof.

Pharmacologically acceptable salts of bisphosphonates and COX-2 inhibitors are preferably salts with bases, conveniently metal salts derived from groups Ia, Ib, IIa and IIb of the Periodic Table of the Elements, including alkali metal salts, e.g. potassium and especially sodium salts, or alkaline earth metal salts, preferably calcium or magnesium salts, and also ammonium salts with ammonia or organic amines.

Especially preferred pharmaceutically acceptable salts of the N-bisphosphonates are those where one, two, three or four, in particular one or two, of the acidic hydrogens of the bisphosphonic acid are replaced by a pharmaceutically acceptable cation, in particular sodium, potassium or ammonium, in first instance sodium.

A very preferred group of pharmaceutically acceptable salts of the N-bisphosphonates is characterized by having one acidic hydrogen and one pharmaceutically acceptable cation, especially sodium, in each of the phosphonic acid groups.

An alternative class of cox-2 inhibitors compounds for use in the invention is the methane sulfonanilide class of inhibitors, of which NS-398, flosulide, nimesulide and (i) are example members.

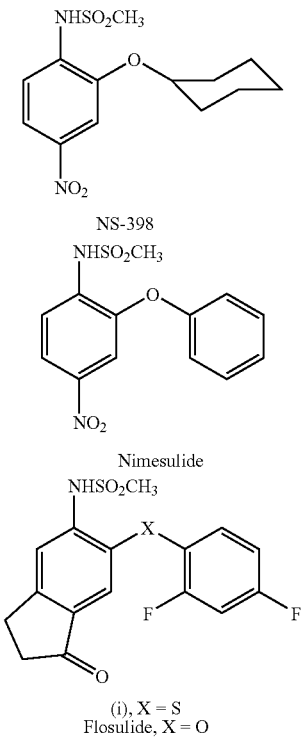

A further class of COX-2 inhibitors is the tricyclic inhibitor class, which can be further divided into the sub-classes of tricyclic inhibitors with a central carbocyclic ring (examples include SC-57666, 1 and 2; those with a central monocyclic heterocyclic ring (examples include DuP 697, SC-58125, SC-58635, SC 236 and 3,4 and 5); and those with a central bicyclic heterocyclic ring (examples include 6, 7, 8, 9 and 10). Compounds 3, 4, and 5 are described in U.S. Pat. No. 5,474,995.

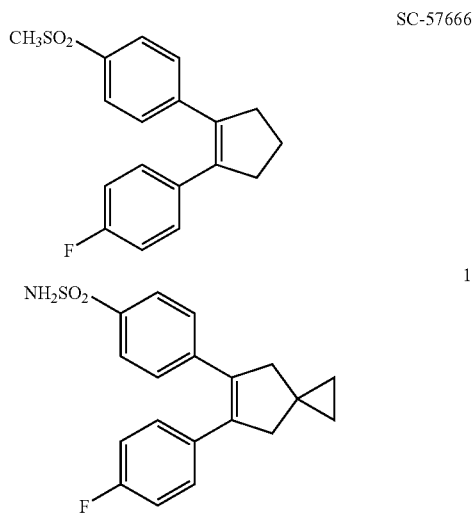

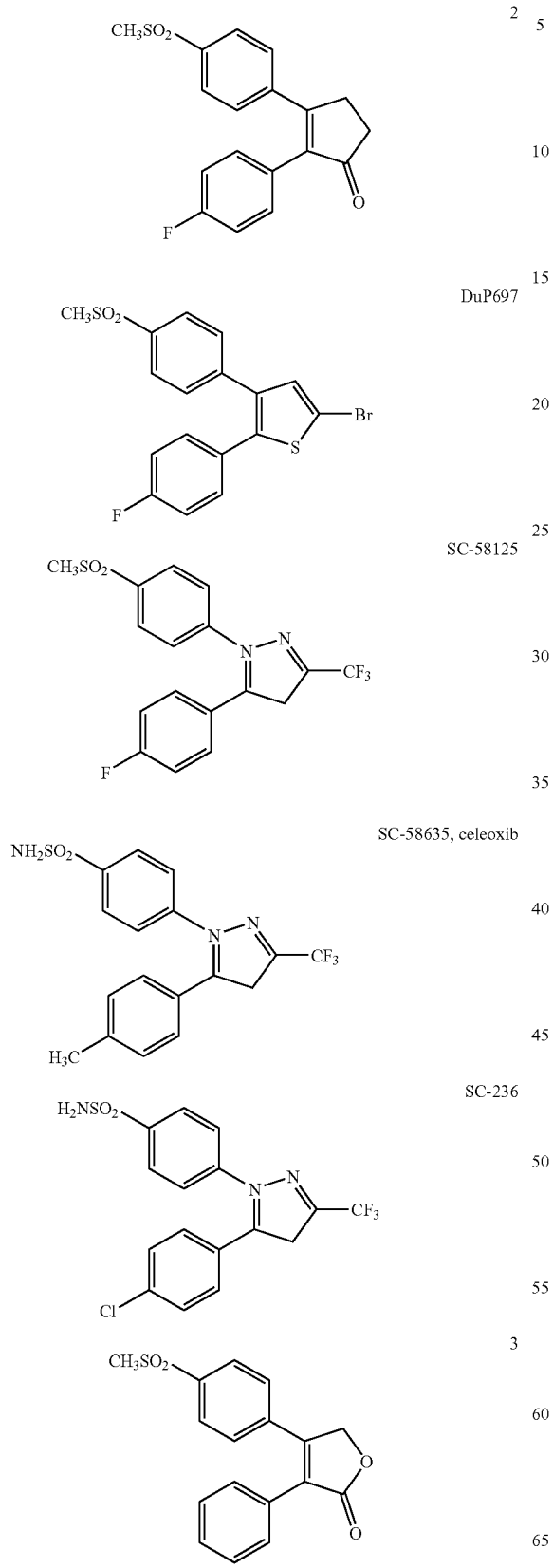
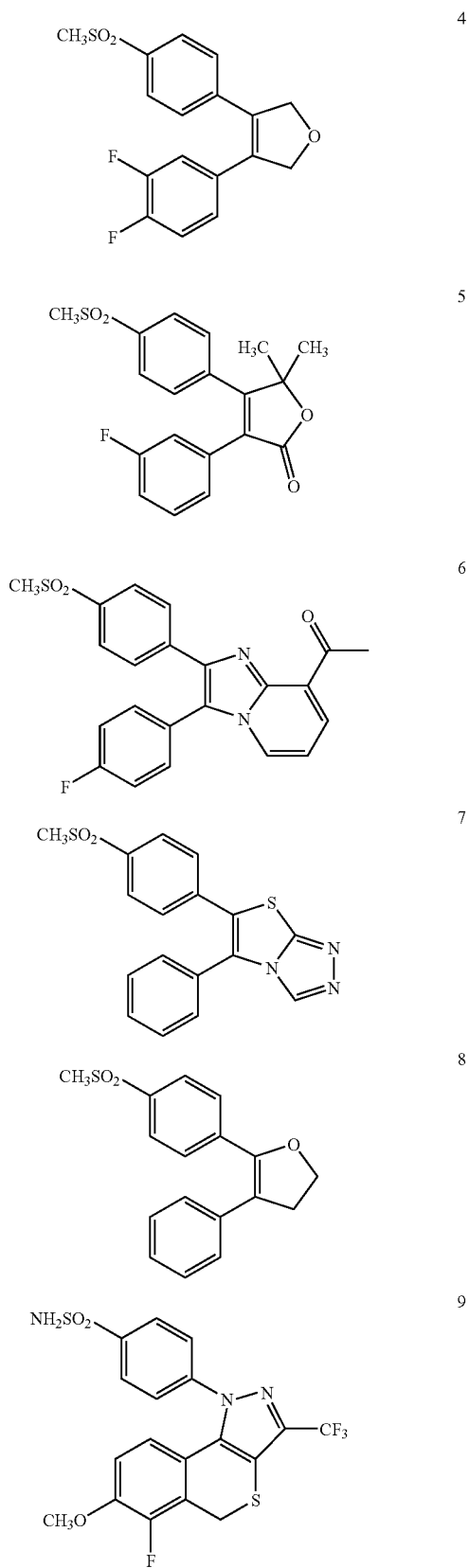

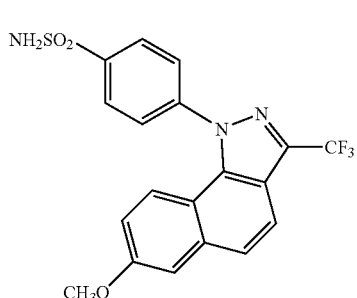

10

A yet further class of COX-2 inhibitors can be referred to as those which are structurally modified NSAIDS, and includes 11a and structure 11 as example members.

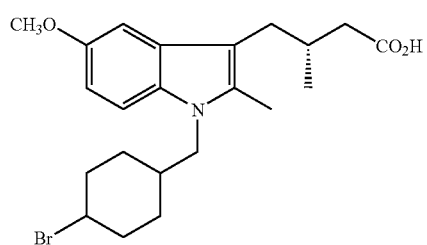

11a

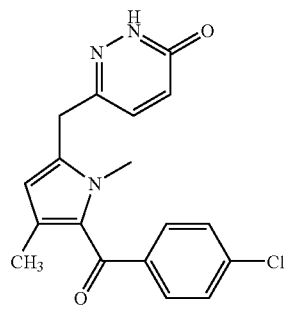

11b

In addition to the structural classes, sub-classes, specific COX-2 inhibitors compound examples, examples of compounds which selectively inhibit cyclooxygenase-2 have also been described in the following patent publications, all of which are herein incorporated by reference: U.S. Pat. Nos. 5,344,991, 5,380,738, 5,393,790, 5,409,944, 5,434,178, 5,436,265, 5,466,823, 5,474,995, 5,510,368, 5,536,752, 5,550,142, 5,552,422, 5,604,253, 5,604,260, 5,639,780; and International Patent Specification Nos. 94/13635, 94/15932, 94/20480, 94/26731, 94/27980, 95/00501, 95/15316, 96/03387, 96/03388, 96/06840; and International Publication No.'s WO 94/20480, WO 96/21667, WO 96/31509, WO 96/36623, WO 97/14691, WO 97/16435.

Additional COX-2 inhibitor compounds which are included in the scope of this invention include.

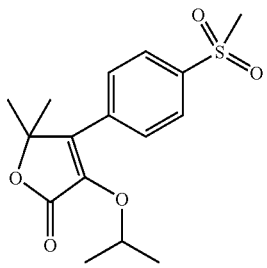

12

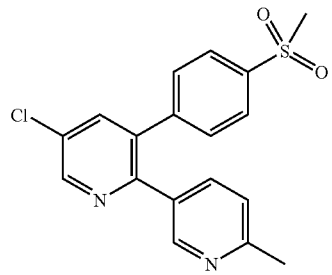

13

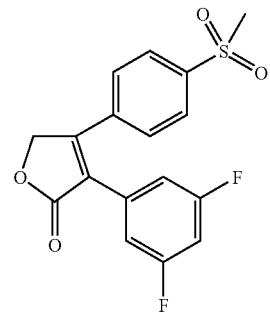

14

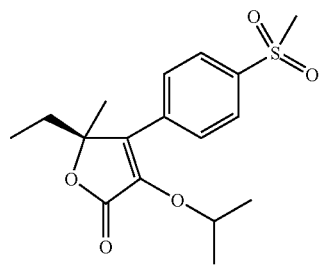

15

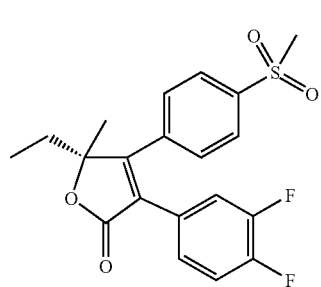

16

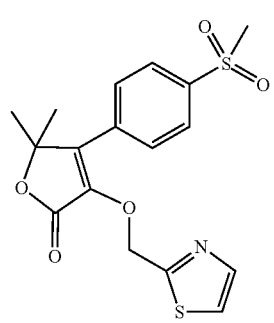

17

18

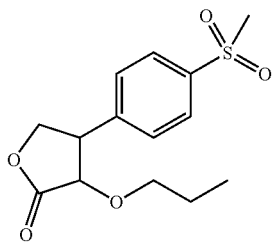

19

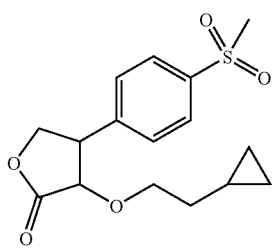

20

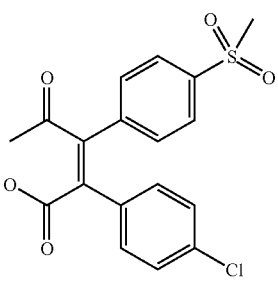

21

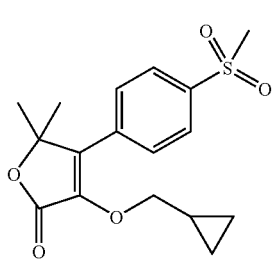

22

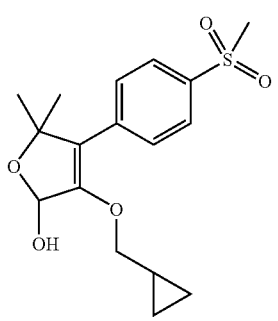

23

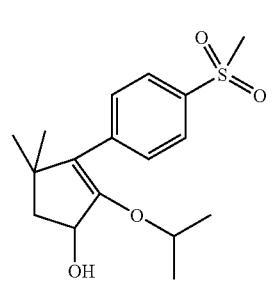

24

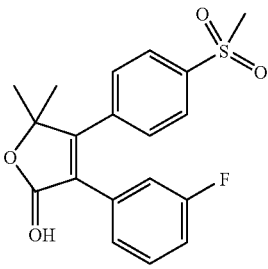

25

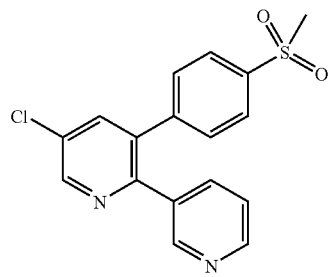

Some of the compounds above can also be identified by the following chemical names:

3: 3-phenyl(4-(methylsulfonyl)phenyl)-2-(5H)-furanone;
4: 3-(3,4-difluorophenyl)-4-(4-(methylsulfonyl)phenyl)-2-(5H)-faranone;
5: 5,5-dimethyl-4-(4-(methylsulfonyl)phenyl)-3-(3-fluorophenyl)-H-furan-2-one;
12: 5,5-dimethyl-4-(4(methylsulfonyl)phenyl)-3-(2-propoxy)-5H-furan-2-one;
13: 5-chloro-3-(4-(methylsulfonyl)phenyl)-2-(2-methyl-5-pyridinyl)pyridine;
14: 2-(3,5-difluorophenyl)-3-(4-(methylsulfonyl)phenyl)-2-cyclopenten-1-one;
15: 5(S)-5-ethyl-5-methyl-4-(4-methylsulfonyl)phenyl)-3-(2-propoxy)-5H-furan-2-one;
16: 5-ethyl-5-methyl-4-(4-(methylsulfonyl)phenyl)-3-(3,4-difluorophenyl)-5H-furan-2-one;
17: 3-((2-thiazolyl)methoxy)-4-(4-methylsulfonyl)phenyl)-5,5-dymethyl-5H-furan-2-one;
18: 3-propyloxy-4-(4-methylsulfonyl)phenyl)-5,5-dimethyl-5H-furan-2-one;
19: 3-(1-cyclopropylethoxy)-5,5-dimethyl-4-(4-methylsulfonyl)phenyl)-5H-furan-2-one;
20: sodium 2-(4-chlorophenyl)-3-(4-methylsulfonyl)phenyl)-4-oxo-2-pentenoate;
21: 3-(cyclopropylmethoxy)-5,5-dimethyl-4(4-methylsulfonyl)phenyl)-5H-furan-2-one;
22: 3-(cyclopropylmethoxy)-5,5-dimethyl-4-(4-methylsulfonyl)phenyl)-2,5-dihydrofuran-2-ol;
23: 33-isopropoxy-5,5-dimethyl-4-(4-methylsulfonyl)phenyl)-2,5-dihydrofuran-2-ol;
24: 5,5-dimethyl-3-(3-fluorophenyl)-2-hydroxy-4-(4-methylsulfonyl)phenyl)-2,5-dihydrofuran;
25: 5-Chloro-3-(4-methylsulfonyl)phenyl)-2-(3-pyridinyl)pyridine.

The following publications describe and/or provide methods for making the compounds as indicated: compounds 12, 15, 17, 18, 19 and 21, WO 97/14691; compounds 22, 23 and 24, WO 97/16435; compound 20, WO 96/36623; compound 14, U.S. Pat. No. 5,536,752; compound 16, U.S. Pat. No. 5,474, 995. See Examples herein for compounds 13 and 25. Also incorporated herein by reference are those compounds described in WO 96/41645 as having structural Formula VI, shown below, and the definition and preferred definitions and species described therein:

VI

Particulary preferred compounds of formula (VI) include:
  5-(4-fluorophenyl)-1-[4-(methylsulfonyl)phenyl]-3-(trifluoromethyl)pyrazole;
  4-(4-fluorophenyl)-5-[4-(methylsulfonyl)phenyl]-1-phenyl-3-(trifluoromethyl)pyrazole;
  4-(5-(4-chlorophenyl)-3-(4-methodoxyphenyl)-1H-pyrazol-1-yl)benzenesulfonamide;
  4-(3,5-bis(4-methylphenyl)-1H-pyrazol-1-yl)benzenesulfonamide;
  4-(5-(4-chlorophenyl)-3-phenyl-1H-pyrazol-1-yl)benzenesulfonamide;
  4-(3,5-bis(4-methoxyphenyl)-1H-pyrazol-1-yl)benzenesulfonamide;
  4-(5-(4-chlorophenyl)-3-(4-methylphenyl)-1H-pyrazol-1-yl)benzenesulfonamide;
  4-(5-(4-chlorophenyl)-3-(4-nitrophenyl)-1H-pyrazol-1-yl)benzenesulfonamide;
  4-(5-(4-chlorophenyl)-3-(5-chloro-2-thienyl)-1H-pyrazol-1-yl)benzenesulfonamide;
  4-(4-chloro-3,5-diphenyl-1H-pyrazol-1-yl)benzenesulfonamide;
  4-(5-(4-chlorophenyl)-3-(trifluoromethyl)-1H-pyrazol-1-yl)benzenesulfonamide;
  4-(5-phenyl)-3-(trifluormethyl)-1H-pyrazol-1-yl)benzenesulfonamide;
  4-(5-(4-fluorphenyl)-3-(trifluoromethyl)-1H-pyrazol-1-yl)benzenesulfonamide;
  4-(5-(4-methoxyphenyl)-3-(trifluormethyl)-1H-pyrazol-1-yl)benzenesulfonamide;
  4-(5-(4-chlorophenyl)-3-(difluoromethyl)-1H-pyrazol-1-yl)benzenesulfonamide;
  4-(5-(4-methylphenyl)-3-(trifluoromethy)-1H-pyrazol-1-yl)benzenesulfonamide;
  4-(4-chloro-5-(4-chlorohenyl)-3-(trifluoromethyl)-1H-pyrazol-1-yl)benzenesulfonamide;
  4-(3-(difluoromethyl)-5-(4-methylphenyl)-1H-pyrazol-1-yl)benzenesulfonamide;
  4-(3-(difluoromethyl)-5-phenyl-1H-pyrazol-1-yl)benzenesulfonamide;
  4-(3-(difluoromethyl)-5-(4-methoxyphenyl)-1H-pyrazol-1-yl)benzenesulfonamide;
  4-(3-cyano-5-(4-fluorophenyl)-1H-pyrazol-1-yl)benzenesulfonamide;
  4-(3-(difluoromethyl)-5-(3-fluoro-4-methodoxyphenyl)-1H-pyrazol-1-yl)benzenesulfonamide;
  4-(5-(3-fluoro-4-methoxyphenyl)-3-(trifluormethyl)-1H-pyrazol-1-yl)benzenesulfonamide;
  4-(4-chloro-5-phenyl-1H-pyrazol-1-yl)benzenesulfonamide;
  4-(5-(4-chlorophenyl)-3-hydroxyphenyl)-1H-pyrazol-1-yl)benzenesulfonamide;
  4-(5-(N,N-dimethylaimio)phenyl)-3-(trifluoromethyl)-1H-pyrazol-1-yl)benzenesulfonamide;
  5-(4-fluorophenyl)-6-(4-(methylsulfonyl)phenyl)spiro[2.4]hept-5-ene;
  4-(6-(4-fluorophenyl)spiro[2.4]hept-5-en-5yl)benzenesulfonamide;
  6-(4-fluorophenyl)-7-(4(methylsulfonyl)phenyl)spiro[3.4]oct-6-ene;
  5-(3-chloro-4-methoxyphenyl)-6-(4-(methylsulfonyl)phenyl)spiro[2.4]hept-5-ene;
  4-(6-(3-chloro-4methoxyphenyl)spiro[2.4]hept-5-en-5-yl)benzenesulfonamide;
  5-(3,5-dichloro-4-methodoxyphenyl)-6-(4-(methylsulfonyl)phenyl)spiro[2.4]hept-5-ene;
  5-(3-chloro-4-fluorophenyl)-6-(4-(methylsulfonyl)phenyl)spiro[2.4]hept-5-ene;
  4-(6-(3,4-dichlorophenyl)spiro[2.4]hept-5-en-5-yl)benzenesulfonamide;
  2-(3-chloro-4-fluorophenyl)-4-(4-fluorophenyl)-5-(4-methylsulfonylphenyl)thiazole;
  2-(2-chlorophenyl)-4-(4-fluorophenyl)-5-(4-methylsulfonylphenyl)thiazole;
  5-(4-fluorophenyl)-4-(4-methylsulfonylphenyl)-2-methylthiazole;
  4-(4-fluorophenyl)-5-(4-methylsulfonylphenyl)-2-trifluormethylthiazole;
  4-(4-fluorophenyl)-5-(4-methylsulfonylphenyl)-2-(2-thienyl)thiazole;
  4-(4-fluorophenyl)-5-(4-methylsulfonylphenyl)-2-benzenesulfonamide;
  4-(4-fluorophenyl)-5-(4-methylsulfonylphenyl)-2-(1-propylamino)thiazole;
  2-((3,5-dichlorophenoxy)methyl)4-(4-fluorophenyl)-5-(4-(methylsulfonyl)phenyl)thiazole;
  5-(4-fluorophenyl)-4-(4-methylsulfonylphenyl)-2-trifluoromethylthiazole;
  1-methylsulfonyl-4-(1,1-dimethyl-4-(4-fluorophenyl)cyclopenta-2,4-dien-3-yl)benzene;
  4-(4-(4-(fluorophenyl-1,1-dimethylcyclopenta-2,4-dien-3-yl)benzenesulfonamide;
  5-(4-fluorophenyl)-6-(4-(methylsulfonyl)phenyl)spiro[2.4]hepta-4,6-diene;
  4-(6-(4-fluorophenyl)spiro[2.4]hepta-4,6-dien-5-yl)benzenesulfonamide;
  6-(4-fluorophenyl)-2-methoxy-5-(4-(methylsulfonyl)phenyl)-pyridine-3-carbonitrile;
  2-bromo-6-(4-fluorophenyl)-5-(4-(methylsulfonyl)phenyl)-pyridine-3-carbonitrile;
  6-(4-fluorophenyl)-5-(4-(methylsulfonyl)phenyl)-2-phenyl-pyridine-3-carbonitrile;
  4-(2-(4-methylpyridin-2-yl)-4-(trifluoromethyl)-1H-imidazol-1-yl)benzenesulfonamide;
  4-(2-(5-methylpyridin-3-yl)-4-(trifluoromethyl)-1H-imidazol-1-yl)benzenesulfonamide;
  4-(2-(2-methylpyridin-3-yl)-4-(trifluoromethyl) 1H-imidazol-1-yl)benzenesulfonamide;
  3-(1-(4-(methylsulfonyl)phenyl)-4-(trifluoromethyl)-1H-imidazol-2-yl)benzenesulfonamide;
  2-(1-(4-(methylsulfonyl)phenyl)-4-(trifluoromethyl)-1H-imidazol-2-yl)pyridine;
  2-methyl-4-(1-(4-(methylsulfonyl)phenyl)-4-(trifluormethyl)-1H-imidazol-2-yl)pyridine;
  2-methyl-6-(1-(4-(methylsulfonyl)phenyl)-4-(trifluormethyl)-1H-imidazole-2-yl)pyridine;
  4-(2-(6-methylpyridin-3-yl)-4-(trifluoromethyl)-1H-imidazol-1-yl)benzenesulfonamide;
  2-(3,4-difluorophenyl)-1-(4-(methylsulfonyl)phenyl)-4-(trifluoromethyl)-1H-imidazole;
  4-(2-(4-methylphenyl)-4-(trifluoromethyl)-1H-imidazol-1-yl)benzenesulfonamide;

2-(4-chlorophenyl)-1-(4-methylsulfonyl)phenyl)-4-methyl-1H-imidazole;
2-(4-chlorophenyl)-1-(4-(methylsulfonyl)phenyl)-4-phenyl-1H-imidazole;
2-(4-chlorophenyl)-4-(4-fluorophenyl)-1-(4-(methylsulfonyl)phenyl)-1H-imidazole;
2-(3-fluoro-4-methoxyphenyl)-1-(4-(methylsulfonyl)phenyl)-4-(trifluoromethyl)-1H-imidazole;
1-(4-methylsulfonyl)phenyl)-2-phenyl-4-trifluoromethyl-1H-imidazole;
2-(4-methylphenyl)-1-(4-(methylsulfonyl)phenyl)-4-trifluoromethyl-1H-imidazole;
4-(2-(3-chloro-4-methylphenyl)-4-trifluoromethyl-1H-imidazol-1-yl)benzenesulfonamide;
2-(3-fluoro-5-methylphenyl)-1-(4-methylsulfonyl)phenyl)-4-(trifluoromethyl)-1H-imidazole;
4-(2-(3-fluoro-5-methylphenyl)-4-(trifluoromethyl)-1H-imidazol-1-yl)benzenesulfonamide;
2-(3-methylphenyl)-1-(4-(methylsulfonyl)phenyl)-4-(trifluoromethyl)-1H-imidazole;
4-(2-(3-methylphenyl)-4-(trifluoromethyl)-1H-imidazol-1-yl)benzenesulfonamide;
1-(4-(methylsulfonyl)phenyl)-2-(3-chlorophenyl)-4-(trifluoromethyl)-1H-imidazole;
4-(2-(3-chlorophenyl)-4-(trifluoromethyl)-1H-imidazol-1-yl)benzenesulfonamide;
4-(2-phenyl-4-(trifluoromethyl)-1H-imidazol-1-yl)benzenesulfonamide;
4-(2-(4-methodxy-3-chlorophenyl)-4-(trifluoromethyl)-1H-imidazol-1-yl) benzenesulfonamide;
1-allyl-4-(4-fluorophenyl)-3-(4-(methylsulfonyl)phenyl)-5-(trifluoromethyl)-1H-pyrazole;
4-(1-ethyl-4-(4-fluorophenyl)-5-(trifluoromethyl)-1H-pyrazol-3-yl)benzenesulfonamide;
N-phenyl-(4-(4-fluorophenyl)-3-(4-(methylsulfonyl)phenyl)-5-(trifluoromethyl)-1H-pyrazol-1-yl)acetamide;
ethyl (4-(4-fluorophenyl)-3-(4-(methylsulfonyl)phenyl)-5-(trifluoromethyl)-1H-pyrazol-1-yl)acetate;
4-(4-fluorophenyl)-3-(4-methylsulfonyl)phenyl)-1-(2-phenylethyl)-1H-pyrazole;
4-(4-fluorophenyl)-3-(4-(methylsulfonyl)phenyl)-1-(2-phenylethyl)-5-(trifluoromethyl)pyrazole;
1-ethyl-4-(4-fluorophenyl)-3-(4-methylsulfonyl)phenyl)-5-(trifluoromethyl)-1H-pyrazole;
5-(4-fluorophenyl)4-(4-methylsulfonyl)phenyl)-2-(trifluoromethyl)-1H-imidazole;
4-(4-methylsulfonyl)phenyl)-5-(2-thiophenyl)-2-(trifluoromethy)-1H-imidazole;
5-(4-fluorophenyl)-2-methodoxy4(methylsulfonyl)phenyl)-6-(trifluoromethyl)pyridine;
2-ethoxy-5-(4-fluorophenyl)-4-(4-(methylsulfonyl)phenyl)-6-(trifluoromethyl)pyridine;
5-(4-fluorophenyl)4-(4-(methylsulfonyl)phenyl)-2-(2-propynyloxy)-6-(trifluoromethyl)pyridine;
2-bromo-5-(4-fluorophenyl)-4-(4-methylsulfonyl)phenyl)-6-(trifluoromethyl)pyridine;
4-(2-(3-chloro-4-methoxyphenyl)-4,5-difluorophenyl) benzensulfonamide;
1-(4-fluorophenyl)-2-(4-methylsulfonyl)phenyl)benzene;
5-difluoromethyl-4-(4-methylsulfonyl)phenyl)-3-phenyl-isoxazole;
4-(3-ethyl-5-phenylisoxazol-4-yl)benzensulfonamid;
4-(5-difluoromethyl-3-phenylisoxazol-4-yl)benzenesulfonamide;
4-(5-hydroxymethyl-3-phenylisoxazol-4-yl)benzenesulfonamide;
4-(5-methyl-3-phenylisoxazol-4-yl)benzenesulfonamide;
1-(2-(4-fluorophenyl)cyclopenten-1-yl)-4-(methylsulfonyl)benzene;
1-(2-(4-fluoro-2-methylphenyl)cyclopenten-1-yl)-4-(methylsulfonyl)benzene;
1-(2-(4-chlorophenyl)cyclopenten-1-yl)-4-(methylsulfonyl)benzene;
1-(2-(2,4-dichlorophenyl)cyclopenten-1-yl)-4-(methylsulfonyl)benzene;
1-(2-(4-trifluoromethylphenyl)cyclopenten-1-yl)-4-(methylsulfonyl)benzene;
1-(2-(4-methylthiophenyl)cyclopenten-1-yl)-4-(methylsulfonyl)benzene;
1-(2-(4-fluorophenyl)-4,4-dimethylcyclopenten-1-yl)-4-(methylsulfonyl)benzene;
4-(2-(4-fluorophenyl)-4,4-dimethylcyclopenten-1-yl) benzesulfonamide;
1-(2-(4-chlorophenyl)-4,4-dimethylcyclopenten-1-yl)-4-(methylsulfonyl)benzene;
4-(2-(4-chlororophenyl)-4,4-dimethylcyclopenten-1-yl) benzenesulfonamide;
4-(2-(4-fluorophenyl)cyclopenten-1-yl)benzenesulfonamide;
4-(2-(4-chlorophenyl)cyclopenten-1-yl)benzenesulfonamide;
1-(2-(4-methoxyphenyl)cyclopenten-1-yl)-4-(methylsulfonyl)benzene;
1-(2-(2,3-difluorophenyl)cyclopenten-1-yl)-4-(methylsulfonyl)benzene;
4-(2-(3-fluoro-4methodyphenyl)cyclopenten-1-yl)benzenesulfonamide;
1-(2-(3-chloro-4-methoxyphenyl)cyclopenten-1-yl)-4-(methylsulfonyl)benzene;
4-(2-(3-chloro-4-fluorophenyl)cyclopenten-1-yl-benzenesulfonamide;
4-(2-(2-methylpyridin-5-yl)cyclopenten-1-yl)benzenesulfonamide;
ethyl 2-(4-(4-fluorophenyl)-5-(4-methylsulfonyl)phenyl) oxazol-2-yl)-2-benzyl-accetate;
2-(4-(4-fluorophenyl)-5-(4-(methylsulfonyl)phenyl)oxazol-2-yl)acetic acid;
2-(tert-butyl)-4-(4-fluorophenyl)-5-(4-methylsulfonyl) phenyl)oxazole;
4-(4-fluorophenyl)-5-(4-(methylsulfonyl)phenyl)-2-phenyloxazole;
4-(4-fluorophenyl)-2-methyl-5-(4-methylsulfonyl)phenyl)oxazole; and
4-(5-(3-fluoro-4-methoxyphenyl)-2-trifluoromethyl-4-oxazolyl)benzenesulfonamide;
or a pharmaceutically acceptable salt thereof.

The N-bisphosphonates are preferably used in the form of pharmaceutical compositions that contain a therapeutically effective amount of active ingredient optionally together with or in admixture with inorganic or organic, solid or liquid, pharmaceutically acceptable carriers which are suitable for administration.

The N-bisphosphonate pharmaceutical compositions may be, for example, compositions for enteral, such as oral, rectal, aerosol inhalation or nasal administration, compositions for parenteral, such as intravenous or subcutaneous administration, or compositions for transdermal administration (e.g. passive or iontophoretic).

Preferably, the N-bisphosphonate pharmaceutical compositions are adapted to oral or parenteral (especially intravenous, intra-arterial or transdermal) administration. Intravenous and oral, first and foremost intravenous, administration is considered to be of particular importance. Preferably the N-bisphosphonate active ingredient is in a parenteral form, most preferably an intravenous form.

The particular mode of administration and the dosage may be selected by the attending physician taking into account the particulars of the patient, especially age, weight, life style, activity level and disease state as appropriate. Most preferably, however, the N-bisphosphonate is administered intravenously.

The dosage of the N-bisphosphonate for use in the invention may depend on various factors, such as effectiveness and duration of action of the active ingredient, mode of administration, warm-blooded species, and/or sex, age, weight and individual condition of the warm-blooded animal.

Taxol is the compound [2aR-[2aα, 4β, 4αβ, 6β, 9α(αR*, βS*),-11α, 12α, 12aα, 12bα]]-β-(benzoylamino)-α-hydroxybenzenepropanoic acid 6,12b-bis(acetyloxy)-12-(benzoyloxy)-2α,3,4,4a,5,6,9,10,11,12,12a,12b-dodecahydro-4,11-dihydroxy-4a,8,13,13-tetramethyl-5-oxo-7,11-methano-1H-cyclodeca[3,4]benz[1,2-b]oxet-9-yl ester, alternatively known as Paclitaxel, which is an antileukemic and antitumour agent, first isolated as the 1-form from the bark of the Pacific yew tree, *Taxus brevifolia, Taxaceae*. Suitable derivatives of taxol for use in the present invention include taxotere (i.e. the compound [2aR-[2aα, 4β, 4αβ, 6β, 9α(αR*, βS*),-11α, 12α, 12aα, 12bα]]-β-[[(1,1-dimethylethoxy)carbonyl]-amino]-α-hydroxybenzenepropanoic acid 12b-(acetyloxy)-12-(benzoyloxy)-2α,3,4,4a,5,6,9,10,11,12,12a,12b-dodecahydro-4,6,11-trihydroxy--4a,8,13,13-tetramethyl-5-oxo-7,11-methano-1H-cyclodeca[3,4]benz[1,2-b]oxet-9-yl ester, alternatively known as docetaxel), taxanes, taxines (e.g. taxine I, taxine II, taxine A or taxine B) or any other suitable taxol derivative. Taxol and suitable derivatives thereof may be used in combination with a bisphosphonate and a COX-2 inhibitor in the present invention. Taxotere is a preferred taxol derivative for us in the present invention. The taxol or taxol derivative pharmaceutical compositions may be, for example, compositions for enteral such as oral, rectal, aerosol inhalation or nasal administration, compositions for parenteral, such as intravenous or subcutaneous administration, or compositions for transdermal administration (e.g. passive or iontophoretic).

The Agents of the Invention (a. the COX-2 inhibitor and the bisphosphonate or b. The COX-2 inhibitor, the bisphosphonate and Taxol or derivative thereof are preferably used in the form of pharmaceutical preparations that contain the relevant therapeutically effective amount of of each active ingredient (either separately or in combination) optionally together with or in admixture with inorganic or organic, solid or liquid, pharmaceutically acceptable carriers which are suitable for administration. The COX-2 inhibitor and bisphosphonate active ingredients may be present in the same pharmaceutical compositions, though are preferably in separate pharmaceutical compositions. Thus the active ingredients may be administered at the same time (e.g. simultaneously) or at different times (e.g. sequentially) and over different periods of time, which may be separate from one another or overlapping.

The COX-2 pharmaceutical compositions may be, for example, compositions for enteral, such as oral, rectal aerosol inhalation or nasal administration, compositions for parenteral, such as intravenous or subcutaneous administration, or compositions for transdermal administration (e.g. passive or iontophoretic).

Preferably, the COX-2 pharmaceutical compositions are adapted to oral or parenteral (especially oral) administration. Intravenous and oral, first and foremost oral, adminstration is considered to be of particular importance. Preferably the COX-2 inhibitor active ingredient is in oral form.

The particular mode of administration and the dosage may be selected by the attending physician taking into account the particulars of the patient, especially age, weight, life style, activity level etc .

The dosage of the Agents of the Invention may depend on various factors, such as effectiveness and duration of action of the active ingredient, mode of administration, warm-blooded species, and/or sex, age, weight and individual condition of the warm-blooded animal.

More particularly, the pharmaceutical compositions comprise an effective cyclooxygenase-2 inhibiting amount of COX-2 inhibitor or compound of formula I which is substantially free of cyclooxygenase-1 inhibiting activity and of side effects attributed thereto.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Tablets may be either film coated or enteric coated according to methods known in the art.

Suitable formulations for transdermal application include an effective amount of a compound of the invention with carrier. Advantageous carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable formulations for topical application, e.g. to the skin and eyes, include aqueous solutions, suspensions, ointments, creams, gels or sprayable formulations, for example, for delivery by aerosol or the like. Such topical delivery systems will in particular be appropriate for dermal application, e.g. for the treatment of skin cancer, for example, for prophylactic use in creams, lotions sprays and the like The dosage of COX-2 inhibitor administered is dependent on the species of warm-blooded animal (mammal), the body weight, age and individual condition, and on the form of administration. A unit dosage for oral administration to a mammal of about 50 to 70 kg may contain between about 5 and 1000 mg, e.g. from 100-800 mg, preferably 200-400 mg of the active ingredient.

COX-2 inhibitor formulations in single dose unit form contain preferably from about 1% to about 90%, and formulations not in single dose unit form contain preferably from about 0. 1% to about 20%, of the active ingredient. Single dose unit forms such as capsules, tablets or dragées contain e.g. from about 1 mg to about 1000 mg of the active ingredient.

COX-2 inhibitor pharmaceutical preparations for enteral and parenteral administration are, for example, those in dosage unit forms, such as dragées, tablets or capsules and also ampoules. They are prepared in a manner known per se, for example by means of conventional mixing, granulating, confectioning, dissolving or lyophilising processes. For example, pharmaceutical preparations for oral administration can be obtained by combining the active ingredient with solid carriers, where appropriate granulating a resulting mixture, and processing the mixture or granulate, if desired or necessary after the addition of suitable adjuncts, into tablets or dragée cores.

Other orally administrable pharmaceutical preparations are dry-filled capsules made of gelatin, and also soft, sealed capsules made of gelatin and a plasticiser, such as glycerol or sorbitol. The dry-filled capsules may contain the active ingredient in the form of a granulate, for example in admixture with fillers, such as lactose, binders, such as starches, and/or glidants, such as talc or magnesium stearate, and, where appropriate, stabilisers. In soft capsules the active ingredient is preferably dissolved or suspended in suitable liquids, such as fatty oils, paraffin oil or liquid polyethylene glycols, it being possible also for stabilisers to be added.

Parenteral formulations are especially injectable fluids that are effective in various manners, such as intravenously, intramuscularly, intraperitoneally, intranasally, intradermally or subcutaneously. Such fluids are preferably isotonic aqueous solutions or suspensions which can be prepared before use, for example from lyophilised preparations which contain the active ingredient alone or together with a pharmaceutically acceptable carrier. The pharmaceutical preparations may be sterilised and/or contain adjuncts, for example preservatives, stabilisers, wetting agents and/or emulsifiers, solubilisers, salts for regulating the osmotic pressure and/or buffers.

Suitable formulations for transdermal application include an effective amount of the active ingredient with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the active ingredient of the skin of the host at a controlled and predetermined rate over a prolonged period of time, and means to secure the device to the skin.

The following examples are intended to illustrate the invention and are not to be construed as being limitations thereon.

EXAMPLES

A. Formulation Examples

Example 1

| Wet granulated tablet composition | |
| --- | --- |
| Amount per tablet | Ingredient |
| 25 mg | COX-2 inhibitor |
| 79.7 mg | Microcrystalline cellulose |
| 79.7 mg | Lactose monohydrate |
| 6 mg | Hydroxypropyl cellulose |
| 8 mg | Croscarmellose sodium |
| 0.6 mg | Iron oxide |
| 1 mg | Magnesium stearate |

Tablet dose strengths of between 5 and 125 mg can be accomodated by varying total weight, and the ratio of the first three ingredients. Generally it is preferable to maintain a 1:1 ratio for microcrystalline cellulose: lactose monohydrate.

Example 2

| Wet granulated tablet composition | |
| --- | --- |
| Amount per tablet | Ingredient |
| 12.5 mg | COX-2 inhibitor |
| 86 mg | Microcrystalline cellulose |
| 86 mg | Lactose monohydrate |
| 6 mg | Hydroxypropyl cellulose |
| 8 mg | Croscarmellose sodium |
| 0.6 mg | Iron oxide |
| 1 mg | Magnesium stearate |

Example 3

| Wet granulated tablet composition | |
| --- | --- |
| Amount per tablet | Ingredient |
| 10 mg | COX-2 inhibitor |
| 87.2 mg | Microcrystalline cellulose |
| 87.2 mg | Lactose monohydrate |
| 6 mg | Hydroxypropyl cellulose |
| 8 mg | Croscarmellose sodium |
| 0.6 mg | Iron oxide |
| 1 mg | Magnesium stearate |

Example 4

| Wet granulated tablet composition | |
| --- | --- |
| Amount per tablet | Ingredient |
| 5 mg | COX-2 inhibitor |
| 89.7 mg | Microcrystalline cellulose |
| 89.7 mg | Lactose monohydrate |
| 6 mg | Hydroxypropyl cellulose |
| 8 mg | Croscarmellose sodium |

-continued

Wet granulated tablet composition

| Amount per tablet | Ingredient |
|---|---|
| 0.6 mg | Iron oxide |
| 1 mg | Magnesium stearate |

Example 5

Directly compressed tablet composition

| Amount per tablet | Ingredient |
|---|---|
| 25 mg | COX-2 inhibitor |
| 106.9 mg | Microcrystalline cellulose |
| 106.9 mg | Lactose anhydrate |
| 7.5 mg | Croscarmellose sodium |
| 3.7 mg | Magnesium stearate |

Tablet dose strengths of between 5 and 125 mg can be accomodated by varying total tablet weight, and the ratio of the first three ingredients. Generally it is preferable to maintain a 1:1 ratio for microcrystalline cellulose:lactose monohydrate.

Example 6

Directly compressed tablet composition

| Amount per tablet | Ingredient |
|---|---|
| 12.5 mg | COX-2 inhibitor |
| 113.2 mg | Microcrystalline cellulose |
| 113.2 mg | Lactose anhydrate |
| 7.5 mg | Croscarmellose sodium |
| 3.7 mg | Magnesium stearate |

Example 7

Directly compressed tablet composition

| Amount per tablet | Ingredient |
|---|---|
| 10 mg | COX-2 inhibitor |
| 42.5 mg | Microcrystalline cellulose |
| 42.5 mg | Lactose anhydrate |
| 4 mg | Croscarmellose sodium |
| 1 mg | Magnesium stearate |

Example 8

Directly compressed tablet composition

| Amount per tablet | Ingredient |
|---|---|
| 5 mg | COX-2 inhibitor |
| 45 mg | Microcrystalline cellulose |
| 45 mg | Lactose anhydrate |
| 4 mg | Croscarmellose sodium |
| 1 mg | Magnesium stearate |

Example 9

Hard gelatine capsule composition

| Amount per capsule | Ingredient |
|---|---|
| 25 mg | COX-2 inhibitor |
| 37 mg | Microcrystalline cellulose |
| 37 mg | Lactose anhydrate |
| 1 mg | Magnesium stearate |
| 1 capsule | Hard gelatin capsule |

Capsule dose strengths of between 1 and 50 mg can be accomodated by varying total fill weight, and the ratio of the first three ingredients. Generally it is preferable to maintain a 1:1 ratio for microcrystalline cellulose:lactose monohydrate.

Example 10

Oral solution

| Amount per 5 mL | Ingredient |
|---|---|
| 50 mg | COX-2 inhibitor |
| to 5 mL | with Polyethylene oxide 400 |

Example 11

Oral suspension

| Amount per 5 mL dose | Ingredient |
|---|---|
| 101 mg | COX-2 inhibitor |
| 150 mg | Polyvinylpyrrolidone |
| 2.5 mg | Poly oxyethylene sorbitan monolaurate |
| 10 mg | Benzoic acid |
| to 5 mL | with sorbitol solution (70%) |

Suspension dose strengths of between 1 and 50 mg/5 ml can be accomodated by varying the ratio of the first two ingredients.

Example 12

Intravenous infusion

| Amount per 200 mL dose | Ingredient |
|---|---|
| 1 mg | COX-2 inhibitor |
| 0.2 mg | Polyethylene oxide 400 |
| 1.8 mg | Sodium chloride |
| to 200 mL | Purified water |

Example 13

Combination Tablet Preparation

Tablets containing 25.0, 50.0 and 100.0 mg, respectively, of a Taxol and 25 mg COX-2 Inhibitor are prepared as illustrated below:

Table for doses containing from 25-200 mg of Taxol and 25 mg COX-2 inhibitor

|  | Amount mg | | |
| --- | --- | --- | --- |
| Taxol | 25.0 | 80.0 | 200.0 |
| COX-2 inhibitor | 25.0 | 25.0 | 25.0 |
| Microcrystalline cellulose | 37.25 | 100.0 | 175.0 |
| Modified food corn starch | 37.25 | 4.25 | 8.5 |
| Magnesium stearate | 0.50 | 0.75 | 1.5 |

Both active compounds, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of Taxol per tablet, and 25 mg COX-2 inhibitor, per tablet.

Example 14

TABLE 1

| Ingredient | Amount per 200 mg tablet batch (kg) |
| --- | --- |
| Core Granulation | |
| 5-methyl-2-(2'-chloro-6'-fluoroanilino)phenylacetic acid drug substance | 50** |
| Microcrystalline cellulose, NF (PH 101) | 12.85 |
| Lactose monohydrate, NF | 11.65 |
| Croscarmellose sodium, NF | 1 |
| Povidone, USP | 4 |
| Titanium dioxide, USP | 2 |
| Water, purified***, USP | 20.375 |
| Extra-granular Phase | |
| Microcrystalline cellulose, NF (PH 102) | 13 |
| Croscarmellose sodium, NF | 3 |
| Titanium dioxide, USP | 2 |
| Magnesium stearate, NF | 0.5 |
| Coating | |
| Opadry white | 2.801**** |
| Opadry yellow | 2.0**** |
| Opadry red | 0.4**** |
| Opadry black | 0.0504**** |
| Water, purified***, USP | 29.758**** |

**The weight of drug substance is taken with reference to the dried substance (100 per cent) on the basis of the assay value (factorization). The difference in weight is adjusted by the amount of microcrystalline cellulose used.
***Removed during processing.
****Includes a 50% excess for loss during the coating process.

Table 1, above, sets out the formula for a batch of approximately 250,000 immediate release film-coated tablets of 5-methyl-2-(2'-chloro-6'-fluoroanilino)-phenylacetic acid. To make the tablets, titanium dioxide is dispersed in water, followed by the addition of povidone and mixing for 20 minutes to make a povidone/titanium dioxide suspension. The drug substance, lactose, microcrystalline cellulose, and croscarmellose are mixed in a high shear mixer (e.g., a Collette Gral) for 5 minutes to form a drug mixture. The drug mixture is granulated in the high shear mixer with the povidone/titanium dioxide suspension. The suspension is pumped at a rate of 3 kg/min into the drug mixture. The resulting mixture is mixed an additional 90 seconds after all the suspension is added. The wet granulation is dried in a fluid bed dryer, using an inlet air temperature of 50° C. The residual water target is 3.5% (with a permissible range of 2.5-4.5%). The dried granulation is passed through a screen using a mill (oscillator) and a 30 mesh screen. The previous steps are repeated to make a second granulation.

The extra-granular phase titanium dioxide is passed through a 60 mesh hand screen. The dry granulations are mixed with the extra-granular phase microcrystalline cellulose, croscarmellose sodium and titanium dioxide in a twin shell mixer for 300 revolutions to form a penultimate mixture. Magnesium stearate is passed through a 60 mesh hand screen and is mixed with the penultimate mixture in a twin shell mixer for 50 revolutions to form a tableting mixture. The tableting mixture is pressed into tablets using a tablet press and oval punches.

The coating powders (Opadry) are mixed with purified water to make a 15% w/w coating suspension. The tablets are film coated with the coating suspension in a coating pan using 60° C. to 75° C. inlet air temperature.

Table 2 sets out the contents of a 200 mg 5-methyl-2-(2'-chloro-6'-fluoroanilino)phenylacetic acid film-coated tablet.

TABLE 2

| Ingredient | Theoretical amount [mg] | Function |
| --- | --- | --- |
| Core | | |
| 5-methyl-2-(2'-chloro-6'-fluoroanilino)phenylacetic acid drug substance | 200 | Active substance |
| Microcrystalline cellulose (PH 101) | 51.4 | Filler |
| Lactose | 46.6 | Filler |
| Povidone | 16 | Binder |
| Titanium dioxide | 8 | Color |
| Croscarmellose sodium | 4 | Disintegrant |
| Water, purified* | Q.S. | Granulating liquid |
| Extragranular phase | | |
| Microcrystalline cellulose (PH 102) | 52 | Filler |
| Croscarmellose sodium | 12 | Disintegrant |
| Titanium dioxide | 8 | Color |
| Magnesium stearate | 2 | Lubricant |
| Core weight | 400 | |
| Coating | | |
| Opadry white (00F18296) | 7.4676 | Color |
| Opadry yellow (00F12951) | 5.3312 | Color |
| Opadry red (00F15613) | 1.0668 | Color |
| Opadry black (00F17713) | 0.1344 | Color |
| Water, purified* | Q.S. | Coating solvent |
| Total weight | 414 | |

*removed during processing

In addition, the tablet formulations may contain 5-methyl-2-(2'-chloro-6'-fluoroanilino)benzyl alcohol and/or 5-methyl-2-(2'-chloro-6'-fluoroanilino)benzoic acid in an amount between about 0.01 and 2% by weight, more specifically between about 0.1 and 1.

Example 15

Capsules containing coated pellets of active ingredient, for example, disodium pamidronate pentahydrate, as active ingredient:

| Core pellet: | |
|---|---:|
| active ingredient (ground) | 197.3 mg |
| Microcrystalline cellulose | 52.7 mg |
| (Avicel ® PH 105) | 250.0 mg |
| +Inner coating: | |
| Cellulose HP-M 603 | 10.0 mg |
| Polyethylene glycol | 2.0 mg |
| Talc | 8.0 mg |
| | 270.0 mg |
| +Gastric juice-resistant outer coating: | |
| Eudragit ® L 30 D (solid) | 90.0 mg |
| Triethyl citrate | 21.0 mg |
| Antifoam ® AF | 2.0 mg |
| Water | |
| Talc | 7.0 mg |
| | 390.0 mg |

A mixture of disodium pamidronate with Avicel® PH 105 is moistened with water and kneaded, extruded and formed into spheres. The dried pellets are then successively coated in the fluidized bed with an inner coating, consisting of cellulose HP-M 603, polyethylene glycol (PEG) 8000 and talc, and the aqueous gastric juice-resistant coat, consisting of Eudragit® L 30 D, triethyl citrate and Antifoam® AF. The coated pellets are powdered with talc and filled into capsules (capsule size 0) by means of a commercial capsule filling machine, for example Höfliger and Karg.

Example 16

Monolith adhesive transdermal system, containing as active ingredient, for example, 1-hydroxy-2-(Imidazol-1-yl)-ethane-1,1-diphosphonic acid:

Composition:

| polyisobutylene (PIB) 300 | 5.0 g |
|---|---:|
| (Oppanol B1, BASF) | |
| PIB 35000 | 3.0 g |
| (Oppanol B10, BASF) | |
| PIB 1200000 | 9.0 g |
| (Oppanol B100, BASF) | |
| hydrogenated hydrocarbon resin | 43.0 g |
| (Escorez 5320, Exxon) | |
| 1-dodecylazacycloheptan-2-one | 20.0 g |
| (Azone, Nelson Res., Irvine/CA) | |
| active ingredient | 20.0 g |
| Total | 100.0 g |

Preparation:

The above components are together dissolved in 150 g of special boiling point petroleum fraction 100-125 by rolling on a roller gear bed. The solution is applied to a polyester film (Hostaphan, Kalle) by means of a spreading device using a 300 mm doctor blade, giving a coating of about 75 g/m². After drying (15 minutes at 60° C.), a silicone-treated polyester film (thickness 75 mm, Laufenberg) is applied as the peel-off film. The finished systems are punched out in sizes in the wanted form of from 5 to 30 cm² using a punching tool. The complete systems are sealed individually in sachets of aluminised paper.

Example 17

Vial containing 1.0 mg dry, lyophilized 1-hydroxy-2-(imidazol-1-yl)ethane-1,1-diphosphonic acid (mixed sodium salts thereof). After dilution with 1 ml of water, a solution (concentration 1 mg/ml) for i.v. infusion is obtained.

Composition:

| active ingredient (free diphosphonic acid) | | 1.0 mg |
|---|---|---:|
| mannitol | | 46.0 mg |
| Trisodium citrate × 2 H$_2$O | ca. | 3.0 mg |
| water | | 1 ml |
| water for injection | | 1 ml. |

In 1 ml of water, the active ingredient is titrated with trisodium citrate×2 H$_2$O to pH 6.0. Then, the mannitol is added and the solution is lyophilized and the lyophilisate filled into a vial.

Example 18

Ampoule containing active ingredient, for instance disodium pamidronate pentahydrate dissolved in water. The solution (concentration 3 mg/ml) is for i.v. infusion after dilution.

Composition:

| active ingredient | 19.73 mg |
|---|---:|
| (≙ 5.0 mg of anhydrous active ingredient) | |
| mannitol | 250 mg |
| water for injection | 5 ml. |

Example 19

Inhibition of growth of human breast cancer cell lines with the combination of zoledronic acid and a COX-2 inhibitor.

Purpose: Cyclo-oxygenase (COX) is prostaglandin H synthase which is the principal enzyme mediating the formation of prostanoids (a collective term for prostacyclins, prostaglandins and thromboxanes). COX-2 is up-regulated in a high percentage of common human cancers and is associated with invasive and metastatic tumor behaviour. COX-2 inhibitors suppress colon cancer growth in vitro by inducing apoptosis. Zoledronic acid, a new generation bisphosphonate used in the treatment of breast cancer-induced bone disease, significantly reduces cell number and induces apoptosis in human breast cancer cells. The purpose of this study was to assess the effect of combining a COX-2 inhibitor with zoledronic acid on breast cancer cell growth.

Methods: The effect of combining the COX-2 inhibitor (SC 236) and zoledronic acid compared to either agent alone was tested in a HER-2/neu transfected human breast cancer cell line (MCF/18) and the control vector transfected line (MCF/neo). Cell number was determined after a 3-day incubation using the MTT tetrazolium dye assay.

Results: Treatment of the HER-2/neu transfected MCF/18 and control MCF/neo cell lines with the SC236 COX-2 inhibitor (1-10 μM) resulted in dose-dependent growth inhibition (15-41% inhibition and 18-53% inhibition, respectively). Treatment with zoledronic acid (1-10 μm) also gave dose-dependent growth inhibition. The HER-2/neu overexpressing MCF/18 cells, however, were less sensitive to zoledronic acid (9-53% inhibition) than the MCF/neo cells (8-67% inhibition). The combination of zoledronic acid (5 µM) and SC 236 (5 µM) appeared to have an enhanced (less than additive) inhibitory effect on the MCF/neo cells and an additive effect on the MCF/18 cells.

Conclusion: Treatment with the COX-2 inhibitor SC236 alone or zoledronic acid alone gave dose-dependent growth inhibition in both a HER-2/neu transfected human breast cancer cell line (MCF/18) and a control vector transfected line (MCF/neo). The MCF/18 line, however, was less sensitive to zoledronic acid. The combination of zoledronic acid with the SC236 COX-2 inhibitor gave an enhanced inhibitory effect on the control MCF/neo breast cancer cells and an additive effect on the HER-2/neu transfected MCF/18 cells compared either agent alone.

Example 20

Inhibition of Growth of Human Breast Cancer Cell Lines with the Combination of a COX-2 Inhibitor, Zoledronic Acid and Docetaxel Docetaxel is an antineoplastic agent belonging to the taxane family. Docetaxel induces bcl-2 phosphorylation and subsequent apoptosis and is effective in the treatment of patients with breast cancer. The purpose of this study was to assess the effect of combining a COX-2 inhibitor with zoledronic acid and/or taxotere on breast cancer cell growth.

Methods: The effect of combining the COX-2 inhibitor (SC236) with zoledronic acid and/or taxotere was tested in a HER-2/neu transfected human breast cancer cell line (MCF/18) and the control vector transfected line (MCF/neo). Cell number was determined after a 3-day incubation using the MTT tetrazolium dye assay.

Results: Treatment of the HER-2/neu transfected MCF/18 and control transfected MCF/neo cell lines with each of the agents resulted in dose-dependent growth inhibition. The HER-2/neu transfected MCF/18 cells, however, were less sensitive to zoledronic acid than the control MCF/neo cells, 9%-53% inhibition and 18%-67% respectively. Treatment with the combination of SC236 (5 µM) and taxotere (2 nM) gave enhanced growth inhibition in the MCF/18 and MCF/neo lines. Treatment with zoledronic acid (5 µM) and taxotere (2 nM) also resulted in enhanced growth inhibition in both cell lines. The combination of SC236 (5 µM) and zoledronic acid (5 µM) had an enhanced inhibitory effect on the MCF/neo cells and an additive effect on the MCF/18 cells. The triple combination of the three agents resulted in a small increase in growth inhibition over and above that seen with any of the double combinations.

Conclusion: All possible double combinations of a COX-2 inhibitor, zoledronic acid and/or a taxotere gave enhanced growth inhibition compared to each agent alone in the MCF/18HER-2/neu tranfected and MCF/neo control vector transfected breast cancer cell lines. The combination of the SC236 COX-2 inhibitor with zoledronic acid was additive in the HER-2/neu transfected cell line. The triple combination resulted in a small increase in growth inhibition over and above that seen with any of the double combinations.

Example 21

Inhibition of Growth of a Human Prostate Cancer Cell Line with the Combination of a COX-2 Inhibitor and Zoledronic Acid Purpose: The purpose of this study was to assess the effect of combining a COX-2 inhibitor with zoledronic acid on prostate cancer cell growth.

Methods: The effect of combining the COX-2 inhibitor (SC236) and zoledronic acid compared to either agent alone was tested in the DU-145 human prostate carcinoma cell line. Cell number was determined after a 3 day treatment using the MTT tetrazolium dye assay.

Results: Treatment with the SC236 COX-2 inhibitor (1-25 µM) resulted in dose-dependent growth inhibition (0-77%). Treatment with zoledronic acid (1-10 µM) also gave dose-dependent growth inhibition (8-70%). The combination of 3 µM zoledronic acid (23% inhibition) and 5 µM SC236 (40% inhibition) resulted in an additive inhibitory effect (60% inhibition) on the DU-145 prostate cell line.

Conclusion: The bisphosphonate, zoledronic acid, and the SC236 COX-2 inhibitor both gave dose-dependent growth inhibition as single agents. Treatment of the DU-145 human prostate carcinoma cell line with the combination of these two agents resulted in an additive inhibitory effect compared to that seen with either agent alone.

The invention claimed is:

1. A pharmaceutical composition for treatment of breast cancer comprises in combination a bisphosphonate; a COX-2 inhibitor, and docetaxel wherein the bisphosphonate is 2-(imidazol-1yl)-1-hydroxyethane-1,1-diphosphonic acid (zoledronic acid) or a pharmacologically acceptable salt thereof and wherein the COX-2 inhibitor is SC236.

2. A method of treating a patient suffering from breast cancer comprising administering to the patient an effective amount of a bisphosphonate, a COX-2 inhibitor and docetaxel wherein the bisphosphonate is 2-(imidazol-1 yl)-1-hydroxyethane-1 , 1-diphosphonic acid (zoledronic acid) or a pharmacologically acceptable salt thereof and wherein the COX-2 inhibitor is SC236.

* * * * *

UNITED STATES PATENT AND TRADEMARK OFFICE
CERTIFICATE OF CORRECTION

PATENT NO. : 7,345,088 B2  Page 1 of 1
APPLICATION NO. : 10/493042
DATED : March 18, 2008
INVENTOR(S) : Green et al.

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 130 days Delete the phrase "by 130 days" and insert -- by 184 days --

Signed and Sealed this

Eleventh Day of November, 2008

JON W. DUDAS
*Director of the United States Patent and Trademark Office*